US012343336B2

(12) United States Patent
Voloshin-Sela (10) Patent No.: US 12,343,336 B2
(45) Date of Patent: Jul. 1, 2025

(54) INCREASING CANCER CELLS' SENSITIVITY TO TUMOR TREATING FIELDS (TTFIELDS) BY INHIBITING IL11 ACTIVITY

(71) Applicant: Novocure GmbH, Root (CH)

(72) Inventor: Tali Voloshin-Sela, Kibbutz Gvat (IL)

(73) Assignee: Novocure GmbH, Baar (CH)

( * ) Notice: Subject to any disclaimer, the term of this patent is extended or adjusted under 35 U.S.C. 154(b) by 1089 days.

(21) Appl. No.: 16/983,241

(22) Filed: Aug. 3, 2020

(65) Prior Publication Data
US 2021/0038584 A1 Feb. 11, 2021

Related U.S. Application Data

(60) Provisional application No. 62/882,813, filed on Aug. 5, 2019.

(51) Int. Cl.
| | | |
|---|---|---|
| A61N 1/00 | (2006.01) |
| A61B 18/12 | (2006.01) |
| A61K 9/00 | (2006.01) |
| A61K 31/4412 | (2006.01) |
| A61N 1/32 | (2006.01) |
| A61N 1/36 | (2006.01) |

(Continued)

(52) U.S. Cl.
CPC .......... *A61K 31/4412* (2013.01); *A61B 18/12* (2013.01); *A61K 9/0019* (2013.01); *A61N 1/32* (2013.01); *A61N 1/36002* (2017.08); *A61P 35/00* (2018.01); *C07K 16/244* (2013.01); *C07K 16/2866* (2013.01); *A61B 2018/00613* (2013.01); *A61K 45/06* (2013.01)

(58) Field of Classification Search
None
See application file for complete search history.

(56) References Cited

U.S. PATENT DOCUMENTS

| | | |
|---|---|---|
| 6,868,289 B2 | 3/2005 | Palti |
| 7,016,725 B2 | 3/2006 | Palti |

(Continued)

FOREIGN PATENT DOCUMENTS

| | | |
|---|---|---|
| WO | 9619574 A1 | 6/1996 |
| WO | 2017078807 A1 | 5/2017 |

OTHER PUBLICATIONS

Gadaleta-Caldarola et al., Sorafenib and locoregional deep electro-hyperthermia in advanced hepatocellular carcinoma: A phase II study (Year: 2014).*

(Continued)

*Primary Examiner* — Sana Sahand
(74) *Attorney, Agent, or Firm* — Potomac Law Group, PLLC (57) ABSTRACT

A reduction in viability of cancer cells (e.g., glioblastoma) and a reduction in tumor volume can be achieved by applying a 100-500 kHz (e.g., 200 kHz) alternating electric field to the cancer cells and inhibiting IL11 (interleukin-11) activity and optionally administering and anti-fibrotic agent. The inhibiting of IL11 activity may be accomplished, for example, by decreasing IL11 expression, inhibiting IL11 signaling, downregulating IL11, neutralizing IL11, blocking an IL11 receptor, administering an IL11 antagonist, administering an IL11 neutralizing antibody, or administering an IL11 receptor α (IL11Ra) neutralizing antibody.

21 Claims, 5 Drawing Sheets

(51) Int. Cl.
*A61P 35/00* (2006.01)
*C07K 16/24* (2006.01)
*C07K 16/28* (2006.01)
*A61B 18/00* (2006.01)
*A61K 45/06* (2006.01)

(56) References Cited

U.S. PATENT DOCUMENTS

| | | |
|---|---|---|
| 7,089,054 B2 | 8/2006 | Palti |
| 7,136,699 B2 | 11/2006 | Palti |
| 7,333,852 B2 | 2/2008 | Palti |
| 7,467,011 B2 | 12/2008 | Palti |
| 7,519,420 B2 | 4/2009 | Palti |
| 7,565,205 B2 | 7/2009 | Palti |
| 7,565,206 B2 | 7/2009 | Palti |
| 7,599,745 B2 | 10/2009 | Palti |
| 7,599,746 B2 | 10/2009 | Palti |
| 7,706,890 B2 | 4/2010 | Palti |
| 7,715,921 B2 | 5/2010 | Palti |
| 7,805,201 B2 | 9/2010 | Palti |
| 7,890,183 B2 | 2/2011 | Palti et al. |
| 7,912,540 B2 | 3/2011 | Palti |
| 7,917,227 B2 | 3/2011 | Palti |
| 8,019,414 B2 | 9/2011 | Palti |
| 8,027,738 B2 | 9/2011 | Palti |
| 8,170,684 B2 | 5/2012 | Palti |
| 8,175,698 B2 | 5/2012 | Palti et al. |
| 8,229,555 B2 | 7/2012 | Palti |
| 8,244,345 B2 | 8/2012 | Palti |
| 8,406,870 B2 | 3/2013 | Palti |
| 8,447,395 B2 | 5/2013 | Palti et al. |
| 8,447,396 B2 | 5/2013 | Palti et al. |
| 8,465,533 B2 | 6/2013 | Palti |
| 8,706,261 B2 | 4/2014 | Palti |
| 8,715,203 B2 | 5/2014 | Palti |
| 10,188,851 B2 | 1/2019 | Wenger et al. |
| 10,441,776 B2 | 10/2019 | Kirson et al. |
| 10,779,875 B2 | 9/2020 | Palti et al. |
| 10,821,283 B2 | 11/2020 | Giladi et al. |
| 11,103,698 B2 * | 8/2021 | Chang .................... A61N 1/025 |
| 2005/0209642 A1 * | 9/2005 | Palti ...................... A61N 1/326 607/2 |
| 2006/0167499 A1 | 7/2006 | Palti |
| 2007/0202106 A1 * | 8/2007 | Palucka ............. A01K 67/0271 435/6.16 |
| 2007/0225766 A1 | 9/2007 | Palti |
| 2007/0239213 A1 * | 10/2007 | Palti ........................ A61N 1/40 607/2 |
| 2009/0076366 A1 | 3/2009 | Palti |
| 2009/0226500 A1 * | 9/2009 | Avelar .................... A61L 31/16 514/183 |
| 2010/0183544 A1 * | 7/2010 | Jenkins .............. A61K 38/2073 424/85.2 |
| 2012/0283726 A1 | 11/2012 | Palti |
| 2013/0184674 A1 | 7/2013 | Palti |
| 2014/0309715 A1 | 10/2014 | Rossi |
| 2014/0330268 A1 | 11/2014 | Palti et al. |
| 2016/0271211 A1 * | 9/2016 | Elliman .................. A61P 37/06 |
| 2017/0120041 A1 | 5/2017 | Wenger et al. |
| 2017/0215939 A1 | 8/2017 | Palti et al. |
| 2017/0281934 A1 | 10/2017 | Giladi et al. |
| 2018/0001075 A1 | 1/2018 | Kirson et al. |
| 2018/0008708 A1 | 1/2018 | Giladi et al. |
| 2018/0050200 A1 | 2/2018 | Wasserman et al. |
| 2018/0160933 A1 | 6/2018 | Urman et al. |
| 2018/0202991 A1 | 7/2018 | Giladi et al. |
| 2018/0362638 A1 | 12/2018 | Cook et al. |
| 2019/0030330 A1 | 1/2019 | Leonhardt et al. |
| 2019/0117956 A1 | 4/2019 | Wenger et al. |
| 2019/0117963 A1 | 4/2019 | Travers et al. |
| 2019/0307781 A1 | 10/2019 | Krex et al. |
| 2019/0308016 A1 | 10/2019 | Wenger et al. |
| 2020/0001069 A1 | 1/2020 | Kirson et al. |
| 2020/0009376 A1 | 1/2020 | Chang et al. |
| 2020/0009377 A1 | 1/2020 | Chang et al. |
| 2020/0016067 A1 | 1/2020 | Gotlib et al. |
| 2020/0023179 A1 | 1/2020 | Bomzon et al. |
| 2020/0038509 A1 * | 2/2020 | Corr ...................... A61B 18/14 |
| 2020/0061360 A1 | 2/2020 | Hagemann et al. |
| 2020/0061361 A1 | 2/2020 | Hagemann et al. |
| 2020/0069937 A1 | 3/2020 | Naveh et al. |
| 2020/0078582 A1 | 3/2020 | Alon et al. |
| 2020/0108031 A1 | 4/2020 | Borst et al. |
| 2020/0121728 A1 | 4/2020 | Wardak et al. |
| 2020/0129761 A1 | 4/2020 | Bomzon et al. |
| 2020/0146586 A1 | 5/2020 | Naveh et al. |
| 2020/0155835 A1 | 5/2020 | Wasserman et al. |
| 2020/0171297 A1 | 6/2020 | Kirson et al. |
| 2020/0179512 A1 | 6/2020 | Giladi et al. |
| 2020/0219261 A1 | 7/2020 | Shamir et al. |
| 2020/0254242 A1 | 8/2020 | Chang et al. |
| 2020/0269037 A1 | 8/2020 | Hagemann et al. |
| 2020/0269041 A1 | 8/2020 | Zeevi et al. |
| 2020/0269042 A1 | 8/2020 | Giladi et al. |
| 2020/0269043 A1 | 8/2020 | Wasserman et al. |
| 2020/0306531 A1 | 10/2020 | Tran et al. |
| 2020/0330755 A1 | 10/2020 | Wasserman et al. |

OTHER PUBLICATIONS

Branter et al., "Tumour treating fields in a combinational therapeutic approach," Oncotarget, vol. 9, No. 93, pp. 36631-36644, Nov. 2018.
Carlson et al., "Numerical stimulation of tumor treating fields effects on cell structures: Mechanism and signaling pathway candidates," Proceedings of the 110th Annual Meeting of the American Association for Cancer Research, Mar. 29-Apr. 3, 2019, Atlanta, Georgia, Abstract nr3725.
Diamant et al., "Evaluating the compatability of tumor treating electric fields with key anti-tumoral immune functions," Proceedings of the 110th Annual Meeting of the American Association for Cancer Research, Mar. 29-Apr. 3, 2019, Atlanta, Georgia, Abstract nr3954.
Giladi et al., "Tumor treating fields (TTFields) delay DNA damage repair following radiation treatment of glioma cells," Radiation Oncology, vol. 12, No. 206, pp. 1-13, 2017.
Giladi et al., "Tumor Treating Fields (TTFields) Delay DNA Damage Repair Following Radiation Treatment of Glioma Cells: Implications for Irradiation Through TTFields Transducer Arrays," International Journal of Radiation Oncology Biology Physics, vol. 99, Issue 2, p. S32, Oct. 2017.
International Search Report and Written Opinion issued in application No. PCT/IB2020/057342 dated Oct. 28, 2020.
Karanam et al., "Exploiting tumor treating fields induced downregulation of BRCA1 pathway for novel combination therapies," Proceedings of the 110th Annual Meeting of the American Association for Cancer Research, Mar. 29- Apr. 3, 2019, Abstract nr3939.
Karanam et al., "Newly identified role of tumor treating fields in DNA damage repair and replication stress pathways," Proceedings of the 109th Annual Meeting of the American Association for Cancer Research, Chicago, Illinois, Apr. 14-18, 2018, Abstract nr3217.
Karanam et al., "Tumor Treating Fields Elicit a Conditional Vulnerability in Non-Small Cell Lung Cancer Lines Through the Down-Regulation of Key DNA Repair and Replication Stress Pathways that When Targeted with Chemoradiation Results in Synergistic Cell Killing," International Journal of Radiation Onocology Biology Physics, vol. 102, No. 3, p. e184, Nov. 2018.
Karanam et al., "Tumor Treatment Fields downregulate specific transcription factors leading to reduced DNA repair capacity, increased replication stress, the inhibition of mitophagy and enhanced cell death," Neuro Onc., vol. 19, Suppl. 6, VI4-VI50, Nov. 2017.
Karanam et al., "Tumor treatment fields downregulate the BRCA1/FA pathway genes leading to reduced DNA repair capacity, the inhibition of mitophagy and enhanced cell death," Cancer Research, vol. 77, Suppl. 13, Abstract nr2138, 2017.
Kirson et al., "Alternating electric fields arrest cell proliferation in animal tumor models and human brain tumors," PNAS, vol. 104, No. 24, pp. 10152-10157, Jun. 2007.

(56) References Cited

OTHER PUBLICATIONS

Krex et al., "Efficacy of Tumor Treating Fields (TTFields) and Aurora B kinase inhibtor," Proceedings of the 109th Annual Meeting of the American Associate for Cancer Research, Apr. 14-18, 2018, Chicago, Illinois, Abstract nr1463.

Lavy et al., "Cancer cell lines response to tumor treating fields: results of a meta-analysis," Neruo. Onc., vol. 20, Suppl. 3, p. i282, Sep. 2018.

Morales et al., "Tumor treating fields (TTFields) significantly alters how tumor cells repair double stranded breaks using homeologous Alu sequences," Proceedings of the 110th Annual Meeting of the American Association for Cancer Research, Mar. 29-Apr. 3, 2019, Atlanta, Georgia, Abstract nr3493.

Schneiderman et al., "Tumor Treating Fields (TTFields) Inhibit Cancer Cell Migration and Invasion by Inducing Reorganization of the Actin Cytoskeleton and Formation of Cell Adhesions," Neuro. Onc., vol. 20, Suppl. 6, p. vi30, Nov. 2018.

Schneiderman et al., "Tumor Treating Fields affect invasion properties and cell morphology of various cancer cells," Neruo Onc., vol. 20, Suppl. 3, p. i282, Sep. 2018.

Shteingauz et al., "Induction of autophagy following TTFields application serves as a survival mechanism mediated by AMPK activation," Proceedings of the 109th Annual Meeting of the American Association for Cancer Research, Apr. 14-18, 2018, Chicago, Illinois, Abstract nr1343,.

Slangen et al., "Cell cycle analysis during TTF to exploit novel targets for increasing treatment efficacy," Proceedings of the 110th Annual Meeting of the American Association for Cancer Research, Mar. 29-Apr. 3, 2019, Atlanta, Georgia, Abstract nr4419.

Story et al., "Exposure to Tumor Treating Fields Inhibits DNA Repair, Induces Replication Stress and Renders Tumor Cells Sensitive to Agents that Impinge Upon These Pathways," Neuro. Onc., vol. 20, Suppl. 6, p. vi30, Nov. 2018.

Tuszynski et al., "An Overview of Sub-Cellular Mechanisms Involved in the Action of TTFields," International Journal of Environmental Research and Public Health, vol. 13, p. 1128, 2016.

Wong et al., "Tumor treating fields exert cellular and immunologic effects," Proceedings ofof the American Association for Cancer Research, Apr. 14-18, 2018, Chicago, Illinois, Abstract.

Chang et al., "Tumor treating fields increases membrane permeability in glioblastoma cells," Cell Death Discovery, 4:113, 2018.

Ghiaseddin et al., "Tumor Treating Fields in the Management of Patients with Malignant Gliomas," Curr. Treat. Options in Oncol., vol. 21, p. 76, Jul. 2020.

Unknown, "Effect of Tumor Treating Fields (TTFields, 150kHz) Concomitant with Sorafenib for Advanced Hepatacellular Carcinoma (HCC) (Hepanova)," ClinicalTrials.gov, ID NCT03606590, Jul. 2019.

Jo et al., "Functional Biological Activity of Sorafenib as a Tumor-Treating Field Sensitizer for Glioblastoma Therapy," International Journal of Molecular Sciences, vol. 19, p. 3684, Nov. 2018.

Putoczki et al., "IL-11 signaling as a therapeutic target for cancer," Immunotherapy, vol. 7, No. 4, pp. 441-453, 2015.

Sommer et al., "Constitutively Active Mutant gp130 Receptor Protein from Inflammatory Hepatocellular Adenoma is Inhibited by an Anti-gp 130 Antibody That Specifically Neutralizes Interleukin 11 Signaling," The Journal of Biological Chemistry, vol. 28, No. 1, pp. 13743-13751, Apr. 2012.

Yang et al., "The inhibition effect of microRNA-23b on proliferation of SMMC-7721 cells through directly targeting IL-11: A clinical study," Journal of Interventional Radiology, vol. 28, No. 4, pp. 358-366, Apr. 2019, Abstract.

\* cited by examiner

INCREASING CANCER CELLS' SENSITIVITY TO TUMOR TREATING FIELDS (TTFIELDS) BY INHIBITING IL11 ACTIVITY

CROSS REFERENCE TO RELATED APPLICATIONS

This Application claims the benefit of US Provisional Application 62/882,813, filed Aug. 5, 2019, which is incorporated herein by reference in its entirety.

BACKGROUND

Tumor Treating Fields, or TTFields, are low intensity (e.g., 1-3 V/cm) alternating electric fields within the intermediate frequency range (e.g., 100-500 kHz) that inhibit cancer cell growth. This non-invasive treatment targets solid tumors and is described in U.S. Pat. No. 7,565,205, which is incorporated herein by reference in its entirety. TTFields are FDA approved for the treatment of glioblastoma (GBM), and may be delivered, for example, via the Optune™ system. Optune™ includes a field generator and two pairs of transducer arrays (i.e., electrode arrays) that are placed on the patient's shaved head. One pair of electrodes is positioned to the left and right of the tumor, and the other pair of electrodes is positioned anterior and posterior to the tumor. In the preclinical setting, TTFields can be applied in vitro using, for example, the Inovitro™ TTFields lab bench system.

SUMMARY OF THE INVENTION

One aspect of the invention is directed to a first method of reducing viability of cancer cells. The first method comprises applying an alternating electric field to the cancer cells, the alternating electric field having a frequency between 100 and 500 kHz; and inhibiting IL11 activity.

In some instances of the first method, the frequency of the alternating electric field is between 180 and 220 kHz. In some instances of the first method, the cancer cells comprise glioblastoma cells and liver cells.

In some instances of the first method, the inhibiting of IL11 activity comprises at least one of decreasing IL11 expression, inhibiting IL11 signaling, downregulating IL11, neutralizing IL11, and blocking an IL11 receptor. In some instances of the first method, the inhibiting of IL11 activity comprises at least one of administering an IL11 antagonist, administering an IL11 neutralizing antibody, and administering an IL11 receptor α (IL11Ra) neutralizing antibody.

In some instances of the first method, a therapeutically effective concentration of a fibrosis inhibitor is administered to the subject. In some instances of the second method, the administering of the fibrosis inhibitor comprises administering at least one of fasudil, pirfenidone, nintedanib, losartan, hyaluronidase, tranilast, and Vismodegib to the subject. In some instances, a therapeutically effective concentration of at least one of a broad spectrum tyrosine kinase inhibitor (e.g., sorafenib, sunitinib and imatinib) is administered to the subject.

Another aspect of the invention is directed to a second method of reducing the volume of a tumor in a body of a living subject. The second method comprises applying an alternating electric field to the tumor, the alternating electric field having a frequency between 100 and 500 kHz; and administering a therapeutically effective concentration of an IL11 inhibitor to the subject.

In some instances of the second method, the frequency of the alternating electric field is between 180 and 220 kHz. In some instances of the second method, at least a portion of the applying step is performed simultaneously with at least a portion of the administering step.

In some instances of the second method, the administering of the IL11 inhibitor comprises administering at least one of an IL11 antagonist, administering an IL11 neutralizing antibody, and administering an IL11 receptor α (IL11Ra) neutralizing antibody.

In some instances of the second method, the administering of the IL11 inhibitor comprises administering at least one of an IL13 antagonist, administering an IL13 neutralizing antibody, and administering an IL13 receptor α (IL13Ra) neutralizing antibody.

In some instances of the second method, a therapeutically effective concentration of a fibrosis inhibitor is administered to the subject.

In some instances of the second method, administering of the fibrosis inhibitor comprises administering at least one of fasudil, pirfenidone, pintedanib, losartan, hyaluronidase, tranilast, and vismodegib to the subject.

In some instances, the second method further comprises administering a therapeutically effective concentration of at least one of a broad spectrum tyrosine kinase inhibitor (e.g., sorafenib, sunitinib and imatinib) to the subject. A tumor volume of the tumor can be reduced by at least about 5 fold.

Another aspect of the invention is directed to a third method of reducing viability of cancer cells disposed in a body of a living subject. The third method comprises applying an alternating electric field to the cancer cells, the alternating electric field having a frequency between 100 and 500 kHz; and administering a therapeutically effective concentration of a fibrosis inhibitor to the subject.

In some instances of the third method, the frequency of the alternating electric field is between 180 and 220 kHz. In some instances of the third method, at least a portion of the applying step is performed simultaneously with at least a portion of the administering step. In some instances of the third method, the administering of the fibrosis inhibitor comprises administering at least one of fasudil, pirfenidone, nintedanib, losartan, hyaluronidase, tranilast, and vismodegib to the subject.

In some instances of the third method, the administering of the fibrosis inhibitor comprises administering a calcium channel blocker to the subject. Optionally, in some of these instances, the calcium channel blocker comprises at least one of Felodipine, Verapamil, Diltiazem, and Nifedipine.

DESCRIPTION OF THE PREFERRED EMBODIMENTS

Ordinarily, most tumors have higher electrical conductivity than healthy surrounding tissue. And this elevated electrical conductivity may explain the specificity of TTFields towards malignant tissue. More specifically, the power loss density of an electric field, L, is defined as $$L = 1/2\sigma|E|^2 \quad \text{equation (1)}$$

where σ is the conductivity of tissue and |E| is the intensity of the electric field. (Power loss density is measured in units of milliwatts per cubic centimeter). And the elevated conductivity 6 within the tumor tissue gives rise to a higher power loss density within that specific tissue.

Clinical data demonstrates a significant increase in IL11 (interleukin-11) expression levels in tumors from GBM patients treated with TTFields. The data was obtained as follows. GBM tumor samples were obtained before and after a treatment according to standard chemoradiation protocol (six patients) or a protocol combining TTFields with standard chemoradiation (six patients). Gene expression analysis was performed by RNA-seq. The negative binomial generalized linear model was used to analyze expression following treatment and the differential effects of control and TTFields treatments. Raw data were analyzed using DESeq2 software. Differential gene expression analysis was calculated using the reads per kilobase million (RPKM) values of chemoradiation and TTFields treatment groups. Statistical analysis was performed using the negative binomial generalized linear model. The difference between expression before and after treatment was derived separately for each individual and the average net treatment effect was calculated for each treatment group. The difference between treatment effects was represented as fold change between the average net effects of TTFields and control. The Benjamini-Hochberg method was used to correct fold change p values for multiple comparisons. A list of 712 genes related to immune activity was compiled using the general literature, the Nanostring "nCounter® PanCancer immune profiling panel" and the ThermoFischer "Oncomine™ immune response" gene lists.

A significant difference between TTFields and control treatment effects was defined as fold change >2 or <0.5 with a corrected p value <0.1. The table below presents the genes that exhibited significantly altered gene expression.

| Gene | Fold change | F.D.R P-val' |
|---|---|---|
| IL11 | 8.5 | 0.001 |
| GPR18 | 5.9 | 0.071 |
| CD70 | 5 | 0.079 |
| CCL26 | 4.5 | 0.031 |
| NKG2D | 4.2 | 0.034 |
| T-bet | 3.4 | 0.019 |
| ICOS-L | 3.3 | 0.094 |
| ISG15 | 3.2 | 0.035 |
| Fac.XII | 3.1 | 0.032 |
| HGF | 3 | 0.041 |
| GNLY | 2.6 | 0.083 |
| MMP2 | 2.5 | 0.036 |

Notably, the differential effects of TTFields+chemoradiation treatments on expression of IL11 (as compared to the chemoradiation-only control) was an 8.5 fold increase. Without being bound by the theory of operation set forth below, this increase in IL11 can cause two problematic issues.

The first problematic issue is that IL11 is known to be a fibrotic factor. As a result, the increase in IL11 associated with the application of TTFields may produce extracellular matrix remodeling and fibrosis within the tumor tissue. Because fibrosis leads to decreased intra- and extra-cellular fluids, fibrotic tissue typically has lower conductivity than non-fibrotic tissue. Therefore, fibrosis that is promoted by the IL11 should (over time) decrease the conductivity 6 in the tumor, which should in turn lower the power loss density in the tumor by operation of equation (1), thereby decreasing the effectiveness of the TTFields. This adverse chain of events can be interrupted by inhibiting IL11 activity. More specifically, inhibiting IL11 activity reduces fibrosis, which allows the conductivity σ to remain high, which allows the power loss density to remain high, which allows the effectiveness of the TTFields to remain high.

The expected effectiveness of interrupting the aforementioned adverse chain of events is supported by experiments establishing that inhibiting IL11 has been shown to prevent heart and kidney fibrosis.

The second problematic issue is that IL11 expression in tumors is associated with an aggressive phenotype and poor prognosis in a large spectrum of tumors including hepatocellular carcinoma, pancreatic cancer, gastric adenocarcinoma, non-small cell lung cancer, breast cancer, endometrial carcinoma, and chondrosarcoma.

Both of the problematic issues noted above can be ameliorated by counteracting the increase in IL11 that occurs when tumors are exposed to TTFields (e.g., by inhibiting IL11 activity).

Examples of some suitable approaches for inhibiting IL11 activity include: decreasing IL11 expression, inhibiting IL11 signaling (e.g., by administering Bazedoxifene), downregulating IL11, neutralizing IL11, blocking an IL11 receptor, administering an IL11 antagonist (e.g., W147A), administering an IL11 neutralizing antibody (e.g., ENx108A, ENx203, or ENx209), and administering an IL11 receptor α (IL11Ra) neutralizing antibody.

Inhibiting IL11 activity may also be accomplished indirectly by inhibiting a stimulator of IL11 or by inhibiting a stimulator of IL11 receptor α (IL11Ra). For example, because IL13 is a potent stimulator of IL11 and IL11Ra, additional examples of suitable approaches for inhibiting IL11 activity include: decreasing IL13 expression, inhibiting IL13 signaling, downregulating IL13, neutralizing IL13 (e.g., by administering Dupilumab), blocking an IL13 receptor, administering an IL13 antagonist, administering an IL13 neutralizing antibody, and administering an IL13 receptor α (IL13Ra) neutralizing antibody.

In view of the above, one approach for treating tumors and reducing viability of cancer cells is to apply TTFields to the cancer cells, and to inhibit IL11 activity. This approach is expected to increase the efficacy of the TTFields treatment by ameliorating both of the problematic issues noted above. In the in vivo context, the inhibition of IL11 activity may be accomplished by administering a therapeutically effective concentration of an IL11 inhibitor to the subject.

An alternative approach for treating tumors and reducing viability of cancer cells is to apply TTFields to the cancer cells, and generically inhibit fibrosis. This approach is expected to increase the efficacy of the TTFields treatment by ameliorating the first problematic issue noted above (without regard to whether the second problematic issue noted above is ameliorated). More specifically, because fibrotic tissue typically has lower conductivity than non-fibrotic tissue, the fibrosis that is triggered by the IL11 should (over time) decrease the conductivity σ in the tumor, which should in turn lower the power loss density in the tumor by operation of equation (1), thereby decreasing the effectiveness of the TTFields. This adverse chain of events can be counteracted by using a different approach for inhibiting the fibrosis that is triggered by the IL11.

In some embodiments, this is accomplished using at least one of the following drugs: fasudil, pirfenidone, nintedanib, losartan, hyaluronidase, tranilast, and vismodegib, (each of which comprises a compound known to inhibit fibrosis). In other embodiments, this is accomplished using a calcium channel blocker that is known to inhibit fibrosis (e.g., Felodipine, Verapamil, Diltiazem, and/or Nifedipine). In other embodiments, this is accomplished using any of a variety of other compounds that are known to inhibit fibrosis.

In some embodiments, this can be accomplished using at least one compound that is both anti-tumorigenic and anti-fibrotic (e.g., sorafenib or any suitable broad spectrum receptor tyrosine kinase inhibitors (RTKI) such as sunitinib and imatinib). In this aspect, sorafenib can decrease fibrosis and decrease tumor size, improving the tumor response to TTFields treatment.

As in the embodiments described above that rely on inhibiting IL11 activity to inhibit fibrosis, the reduction in the level of fibrosis in these embodiments will allow the conductivity σ to remain high, which allows the power loss density to remain high, which allows the effectiveness of the TTFields to remain high.

In the in vivo context, the inhibition of fibrosis may be accomplished by administering a therapeutically effective concentration of a fibrosis inhibitor to the subject.

In the in vivo context, the administering of the relevant molecule or molecules (e.g., an IL11 inhibitor or a fibrosis inhibitor) to the cancer cells can occur continuously from a first time ($t_1$) when the molecule(s) are circulating in the patient's body (e.g., after administering it systemically) or introduced into the vicinity of the cancer cells until such time ($t_2$) as the molecule(s) are eliminated from the patient's body or exhausted. As a result, if TTFields are applied to the cancer cells between $t_1$ and $t_2$, the applying step will be simultaneous with at least a portion of the administering step. The administration of the molecule(s) to the subject may be performed using any of a variety of approaches including but not limited to intravenously, orally, subcutaneously, intrathecal, intramuscularly, intraventricularly, and intraperitonealy. And the application of the alternating electric field to the cancer cells may be performed using the Novocure Optune® system or a variant thereof that operates at a different frequency.

In some instances, fibrosis can be reduced using factors that are both anti-fibrotic and anti-tumorigenic. For example, it is known that the combination of TTFields and sorafenib synergistically reduces tumor volume in hepatocellular carcinoma N1S1 cells. See US Patent Application Publication 2020/0016067; FIG. 1. As shown in FIG. 1, the combination of TTFields and sorafenib results in at least a 10 fold decrease in tumor volume.

Figure 3A:
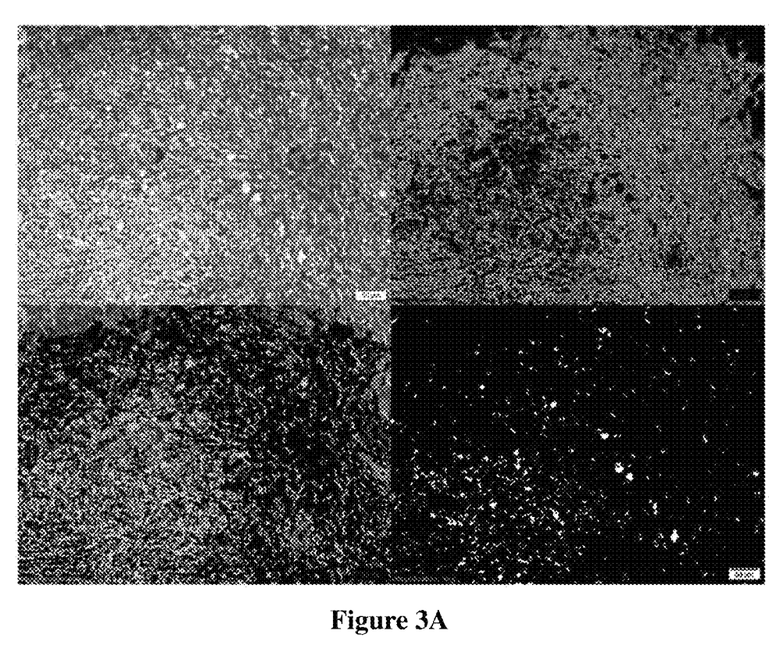
FIG. 3A shows an exemplary histopathological evaluation of the fibrosis specific mason trichrome (MT) stain (blue) of treated N1S1 liver carcinoma tumors showing (1) the original image (used for fibrosis score) (upper left), (2) Color segmentation of fibrosis in MT stained sections with the ROI-blue color representing fibrosis (for area calculation), (3) whole tissue without fibrosis (for area calculation, red-eosin, lower left); and (4) areas outside the tissue (lower right)
Figure 3B:
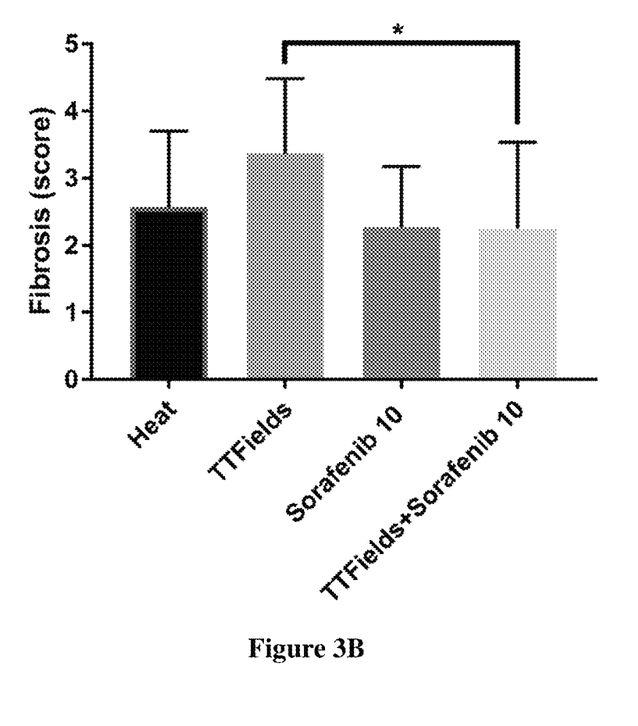
FIG. 3B shows the fibrosis score for the experiment described with respect to FIG. 3A.
Figure 4:
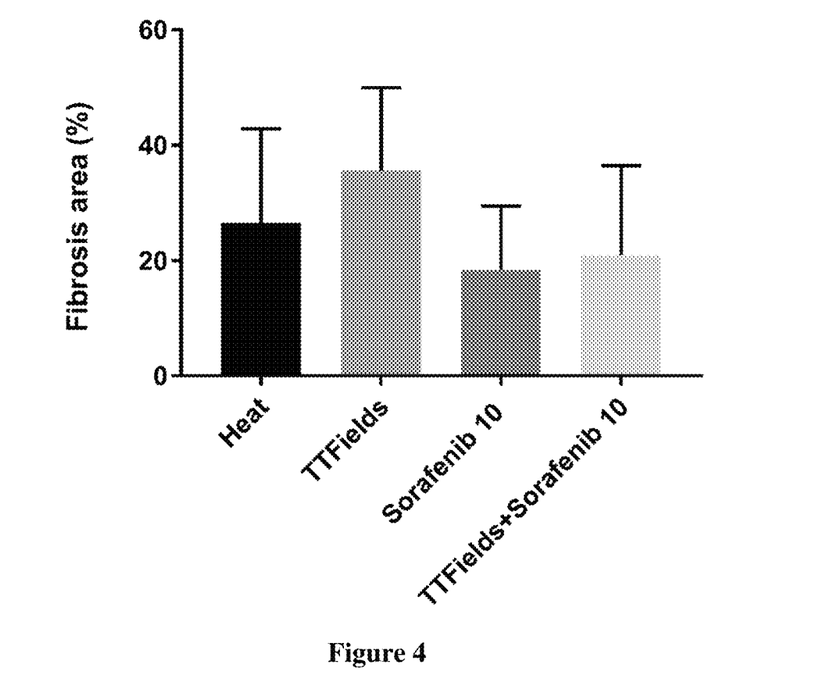
FIG. 4 shows the fibrosis area (%) for each condition calculated from the experiment described with respect to FIG. 3A.
Figure 5:
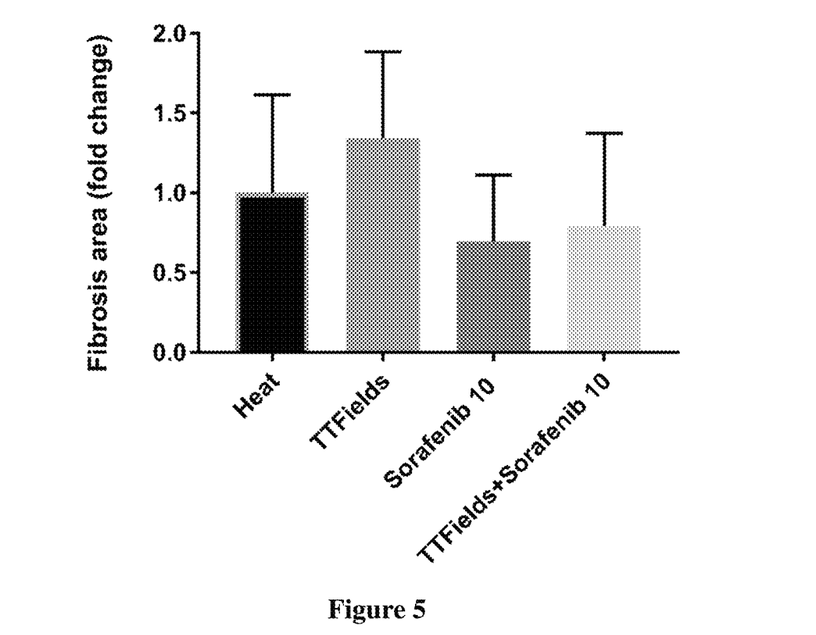
FIG. 5 shows the fibrosis area represented as fold change for each condition as calculated from the experiment described above with respect to FIG. 3A.

The effects of TTFields alone and in combination with sorafenib were evaluated with respect to their impact on fibrosis in N1S1 tumors. TTFields in combination with sorafenib significantly reduced the fibrosis score relative to TTFields alone as evaluated by a pathologist. FIGS. 3A-3B. The fibrosis area of the tumors was measured by percent area and fold change and showed a similar reduction in Fibrosis. FIGS. 4-5.

Figure 6A:
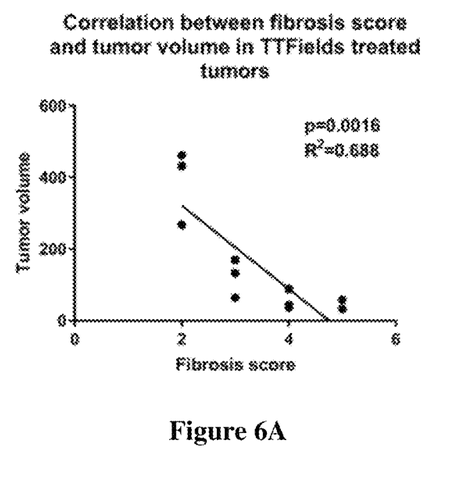
FIGS. 6A-6D show a correlation between (1) the fibrosis score and tumor volume in TTFields treated tumors (FIG. 6A), (2) the fibrosis score and tumor fold change in TTFields treated tumors (FIG. 6B), (3) the fibrosis area and tumor fold change in TTFields treated tumors (FIG. 6C), and (4) the fibrosis area and tumor volume in TTFields treated tumors (FIG. 6D).
Figure 6B:
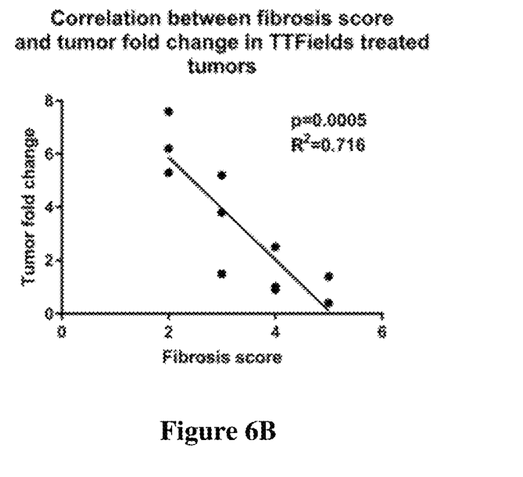
Figure 6C:
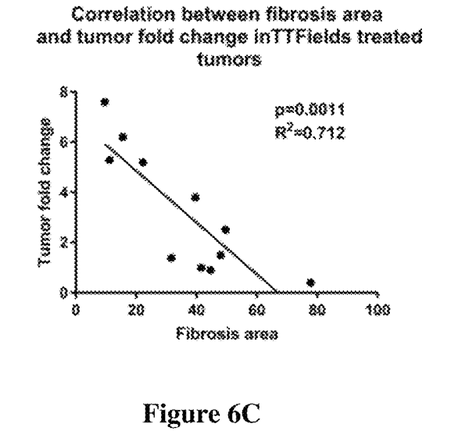
Figure 6D:
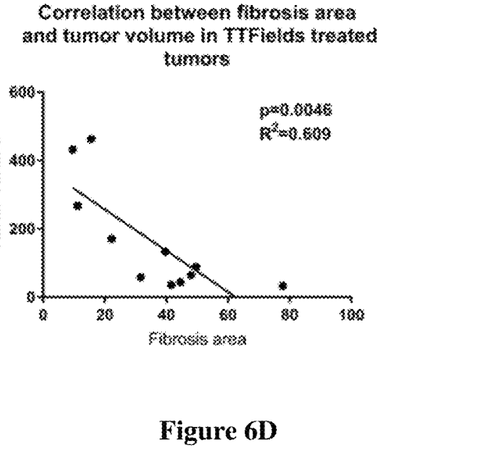

The reduction in tumor fold change (FIG. 1A) and tumor volume (FIG. 1B) correlated with the increase in fibrosis score (FIGS. 6A-6B) in TTFields treated tumors. The reduction in tumor fold change and tumor volume correlated with fibrosis area increase (FIGS. 6C-6D).

Taken together, TTFields can be combined with anti-IL11 and/or additional anti-fibrotic agents and agents that can reduce tumor volume synergistically. In some instances, sorafenib can be used to reduce tumor volume and also as an anti-fibrotic agent as described herein.

The term "reducing viability of cancer cells" as used herein, refers to reducing the growth, proliferation, or survival of the cancer cells. In some aspects, the reduction in viability of the cancer cells comprises reducing clonogenic survival of the cancer cells, increasing cytotoxicity of the cancer cells, inducing apoptosis in the cancer cells, and decreasing tumor volume in a tumor formed from at least a portion of the cancer cells.

The term "clonogenic survival" refers to the ability of a single cancer cell to grow into a colony of cancer cells. In one aspect, a "colony" is at least fifty cells.

The term "cytotoxicity" refers to a measure of the ability of drug or treatment to kill a cell.

The term "apoptosis" refers to the phenomena termed "programmed cell death" referring to the death of cell as part of the controlled cell cycle of cell growth and development.

The term "therapeutically effective concentration," as used herein, refers to the concentration of the relevant compound sufficient to achieve its intended purpose (e.g., inhibiting IL 11 activity, inhibiting fibrosis, etc.).

EXAMPLES

Example 1

Figure 1A:
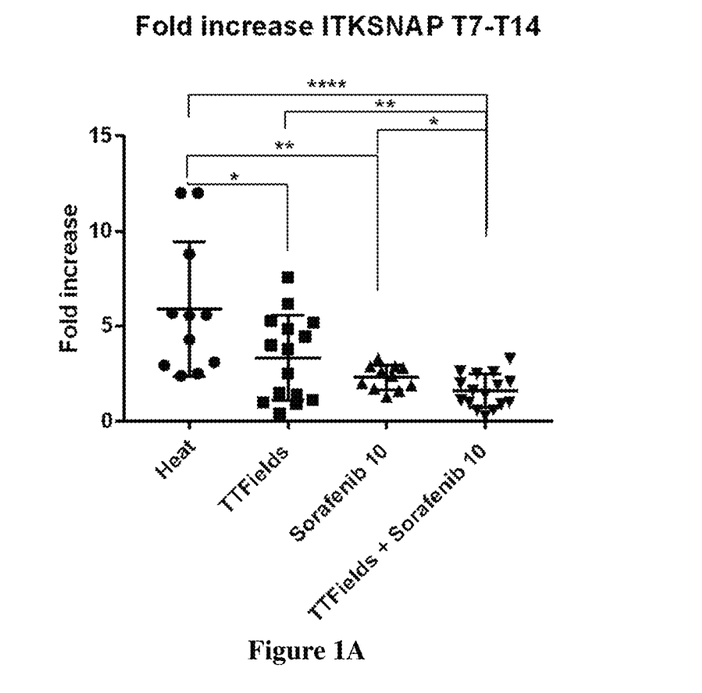
FIGS. 1A-1B show the results of an exemplary study demonstrating the reduction in fold increase of tumor volume and tumor volume, respectively, resulting from the combination of TTFields at 150 kHz and sorafenib in N1S1 liver carcinoma cells.
Figure 1B:
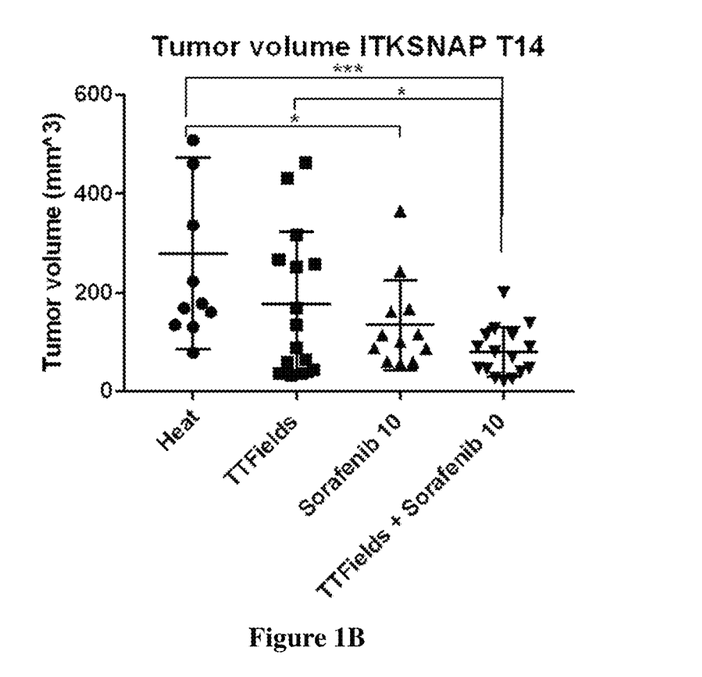

TTFields (150 kHz)/Sorafenib Combination Led to a Significant Reduction in Tumor Volume in Vivo As shown in FIGS. 1A and 1B and in US Patent Application Publication 2020/0016067 (hereby incorporated by reference in its entirety), the combination of TTFields at 150 kHz and sorafenib significantly reduced the fold increase in tumor volume in N1S1 liver carcinoma cells. Tumor volume was determined by MRI. FIGS. 1A and 1B shows the results of an in vivo study described below with respect to N1S1 tumor volume in Sprague Dawley rats treated with heat, TTFields alone, sorafenib alone, and the combination of TTFields and sorafenib. In this experiment, the volume of the tumor was measured using MRI on day 6 (one day before treatment start) and day 14 (one day after the end of treatment); and each data point in FIG. 1A represents the volume of the tumor on day 14 divided by the volume of the tumor on day 6. Thus, numbers greater than 1 represent growth in the tumor volume, and numbers smaller than 1 represent a tumor that has shrunk between day 6 and day 14. In this figure, "*" represents p<0.1, "" represents p<0.01, and "**" represents p<0.0001. As shown in FIG. 1, there is a synergistic decrease in tumor volume following treatment with a combination of TTFields (2.86 V/cm) and sorafenib (10 mg/kg/day). FIG. 1B represents the volume of the tumor.

Example 2

Fibrosis and TTFields Treatment

Figure 2:
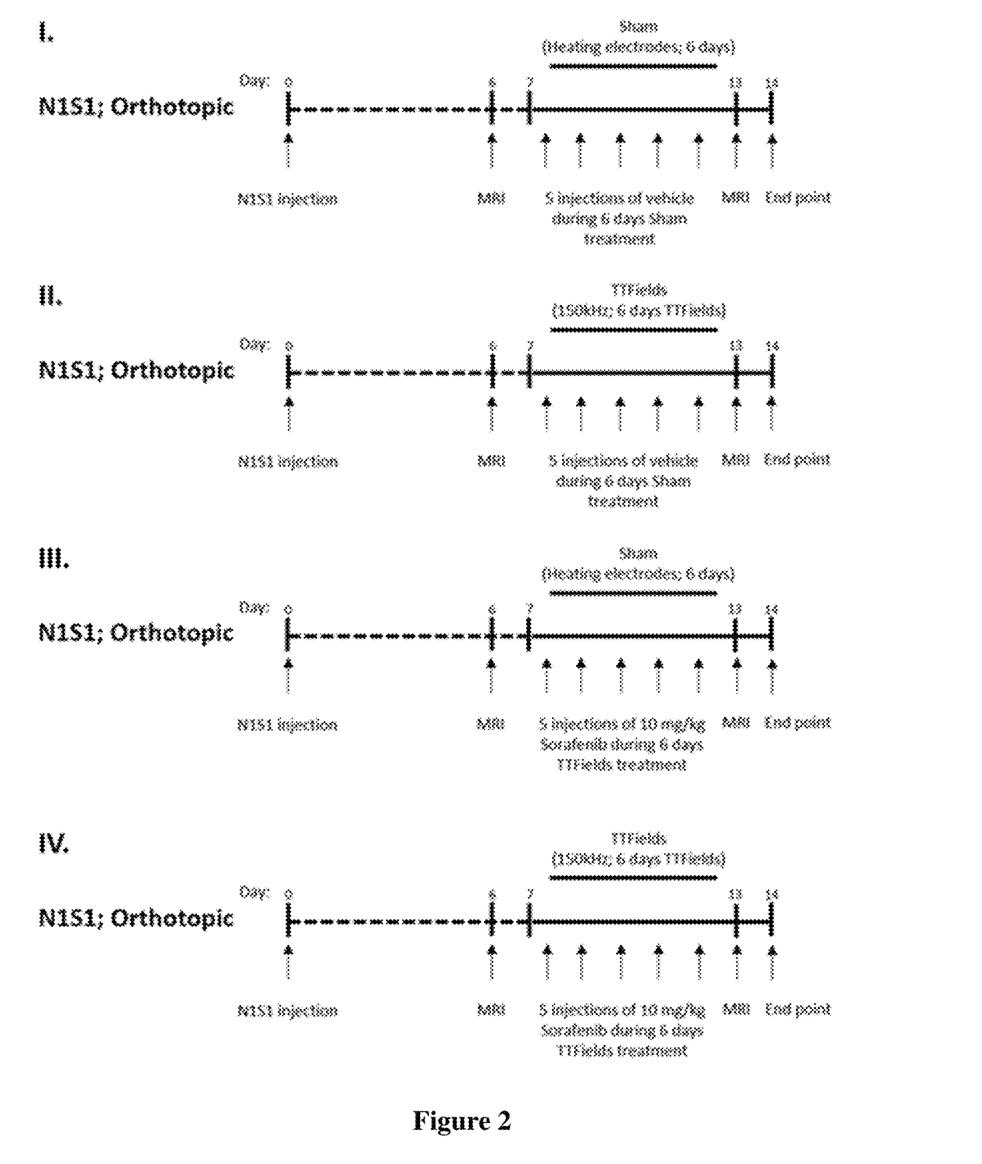
FIG. 2 shows an exemplary TTFields treatment and dosing regimen for four treatment conditions (I, II, II, and IV) to evaluate fibrosis.

Male SD rats, 8-weeks of age (Envigo Ltd, Israel), were anesthetized by I.P. injection of Ketamine (75 mg/kg) and Xylazine (10 mg/kg)(FIG. 2). After loss of postural reflexes, the fur was removed from the upper abdominal area using a trimmer. The left lobe of the liver was surgically exposed and 10 μl of cell suspension containing 50,000 N1-S1 hepatocellular carcinoma cells in equal volumes of serum free medium and Matrigel (CORNING, Bedford, MA) were injected directly into the left lobe using a syringe with a 31-gauge needle. The peritoneum and abdominal muscles incisions were closed using surgical sutures and the skin were close by clips. The rats were allowed to recover for 6 days.

On day 6 all animals underwent a first MRI scan and were randomly divided into the following treatment groups:

Group I—rats were treated with sham heating electrodes and vehicle injection.

Group II—rats were treated with 150 kHz TTFields and vehicle injection.

Group III—rats were treated with 10 mg/kg/day Sorafenib.

Group IV—rats were treated with 150 kHz TTFields and 10 mg/kg/day Sorafenib.

On day 7, electrodes (TTFields or sham heating) were placed on the animals. The animals were treated for 6 days with TTFields or sham heat. Sorafenib or the control vehicle were administered through IP injection on 5 out of 6 days of treatment. On day 13 all electrodes were removed, and the animals underwent a second MRI on day 14 and euthanized. Tumor volume were determined based on MRI scans on days 1 and 14 after tumor implantation. The MRI system is a Bruker Icon system working at 1 Tesla placed inside the animal facility of the company Animals were anesthetized with isoflurane and placed prone in a rat body coil. After a localizer image, a T2 weighted coronal anatomical image were scanned with a RARE sequence and the following parameters: TR/TE 1900/51 ms, number of slices 10, slice thickness 1 mm, FOV 55-65 mm, acquisition matrix 140, 8 averages, acquisition time 4 m 18 s. Tumor volume was measured by manual segmentation of the tumor using ITK-SNAP version 3.6.0-rc1 free software. (t-test; *P<0.05, P<0.01, and *P<0.001)(FIG. 1).

Tumors were harvested for histological evaluation of the grade of fibrosis using a semi-quantitative evaluation scale. Paraffin blocks were sectioned at approximately 4 microns thickness. The sections were put on glass slides and stained with Hematoxylin & Eosin (H&E) and Masson Trichrome (MT). Masson Trichrome stained sections were analyzed for fibrosis, using a scoring grade scale and digital morphometry.

H&E stained sections were examined by one pathologist and scored by a semi-quantitative scoring system for the presence of pathological changes (FIGS. 3 and 3A), as follows:

Grade 0: no signs of fibrosis
Grade 1: very mild signs of fibrosis
Grade 2: mild signs of fibrosis
Grade 3: moderate signs of fibrosis
Grade 4: High grade of fibrosis
Grade 5: Very high grade of fibrosis Color segmentation of blue stained areas (MT: fibrosis) was performed, as demonstrated in FIG. 3, with MATLAB Color-Based Segmentation, using the L*a*b* Color Space. The L*a*b* color space is derived from the CIE XYZ tri-stimulus values. The L*a*b* space consists of a luminosity 'L*' or brightness layer, chromaticity layer 'a*' indicating where color falls along the red-green axis, and chromaticity layer 'b*' indicating where the color falls along the blue-yellow axis.

Example 3

Morphometry (Fibrosis Area Fold Change, Fibrosis Area Percent)

The percent of the stained areas (FIG. 3: top-right) out of the whole tissue (FIG. 3: top-right+bottom-left) was calculated as shown in FIG. 4.

Morphometry of fibrosis percent shows highest fibrotic area in tumors from rats that received TTFields alone (34% increase relative to control), and lowest fibrotic area in tumors from rats that received sorafenib (anti-fibrotic) alone (30.4% decrease relative to control).

The combined treatment of TTFields and sorafenib resulted in 20.8% reduction in fibrotic area compared to control group. These results are summarized in "Fibrosis area (fold change)" (FIG. 5). The percent change in fibrosis area is summarized in FIG. 4.

Example 4

Correlation of Response to TTFields Measured as Tumor Volume Reduction and Increase in Fibrosis FIGS. 6A-6D show a correlation between (1) the fibrosis score and tumor volume in TTFields treated tumors (FIG. 6A), (2) the fibrosis score and tumor fold change in TTFields treated tumors (FIG. 6B), (3) the fibrosis area and tumor fold change in TTFields treated tumors (FIG. 6C), and (4) the fibrosis area and tumor volume in TTFields treated tumors (FIG. 6D). Without being bound by theory, it is believed that reducing fibrosis associated with TTFields treatment makes the tumor more susceptible to treatment with TTFields alone, and in combination with an IL11 inhibitor, fibrosis inhibitor, or an anti-tumorigenic factor/fibrosis inhibitor (e.g., sorafenib).

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method of reducing viability of cancer cells, the method comprising:
   applying an alternating electric field to the cancer cells, the alternating electric field having a frequency between 100 and 500 kHz and an intensity of 1-3 V/cm; and
   inhibiting Interleukin 11 (IL11) activity,
   wherein the cancer cells are at least one of glioblastoma cells, liver cells, pancreatic cancer, non-small cell lung cancer, breast cancer, endometrial carcinoma, or chondrosarcoma.

2. The method of claim 1, wherein the frequency of the alternating electric field is between 180 and 220 kHz.

3. The method of claim 1, wherein the cancer cells are at least one of glioblastoma cells, non-small cell lung cancer, breast cancer, endometrial carcinoma, or chondrosarcoma.

4. The method of claim 1, wherein the inhibiting of IL11 activity comprises at least one of decreasing IL11 expression, inhibiting IL11 signaling, downregulating IL11, neutralizing IL11, and blocking an IL11 receptor.

5. The method of claim 1, wherein the inhibiting of IL11 activity comprises at least one of administering an IL11 antagonist, administering an IL11 neutralizing antibody, and administering an IL11 receptor α (IL11Ra) neutralizing antibody.

6. The method of claim 1, further comprising administering a therapeutically effective concentration of a fibrosis inhibitor to the subject.

7. The method of claim 6, wherein the administering of the fibrosis inhibitor comprises administering at least one of fasudil, pirfenidone, nintedanib, losartan, hyaluronidase, tranilast, and vismodegib to the subject.

8. The method of claim 1, further comprising administering a therapeutically effective concentration of at least one of sorafenib, sunitinib and imatinib to the subject.

9. The method of claim 1, wherein at least a portion of the applying step is performed simultaneously with at least a portion of the inhibiting step.

10. The method of claim 1, further comprising administering a calcium channel blocker to the subject.

11. The method of claim 10, wherein the calcium channel blocker comprises at least one of felodipine, verapamil, diltiazem, and nifedipine.

12. A method of reducing a volume of a tumor in a body of a living subject, the method comprising:
    applying an alternating electric field to the tumor, the alternating electric field having a frequency between 100 and 500 kHz and an intensity of 1-3 V/cm; and
    administering a therapeutically effective concentration of an IL11 inhibitor to the subject, wherein the cancer cells are at least one of glioblastoma cells, liver cells, pancreatic cancer, non-small cell lung cancer, breast cancer, endometrial carcinoma, or chondrosarcoma.

13. The method of claim 12, wherein the frequency of the alternating electric field is between 180 and 220 KHz.

14. The method of claim 12, wherein at least a portion of the applying step is performed simultaneously with at least a portion of the administering step.

15. The method of claim 12, wherein the administering of the IL11 inhibitor comprises administering at least one of an IL11 antagonist, administering an IL11 neutralizing antibody, and administering an IL11 receptor α (IL11Ra) neutralizing antibody.

16. The method of claim 12, wherein the administering of the IL11 inhibitor comprises administering at least one of an IL13 antagonist, administering an IL13 neutralizing antibody, and administering an IL13 receptor α (IL13Ra) neutralizing antibody.

17. The method of claim 12, further comprising administering a therapeutically effective concentration of a fibrosis inhibitor to the subject.

18. The method of claim 17, wherein the administering of the fibrosis inhibitor comprises administering at least one of fasudil, pirfenidone, nintedanib, losartan, hyaluronidase, tranilast, and vismodegib to the subject.

19. The method of claim 12, further comprising administering a therapeutically effective concentration of at least one of sorafenib, sunitinib and imatinib to the subject.

20. The method of claim 19, wherein a tumor volume of the tumor is reduced by at least about 5 fold.

21. The method of claim 12, wherein the cancer cells are at least one of glioblastoma cells, non-small cell lung cancer, breast cancer, endometrial carcinoma, or chondrosarcoma.

* * * * *